United States Patent
Irisawa et al.

(10) Patent No.: US 12,111,314 B2
(45) Date of Patent: Oct. 8, 2024

(54) TEST DEVICE

(71) Applicant: FUJIFILM Corporation, Tokyo (JP)

(72) Inventors: Kaku Irisawa, Ashigarakami-gun (JP); Yoshihiro Seto, Ashigarakami-gun (JP); Hitoshi Shimizu, Ashigarakami-gun (JP); Takahiro Miyato, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 274 days.

(21) Appl. No.: 17/720,774

(22) Filed: Apr. 14, 2022

(65) Prior Publication Data
US 2022/0236263 A1 Jul. 28, 2022

Related U.S. Application Data

(63) Continuation of application No. PCT/JP2020/038808, filed on Oct. 14, 2020.

(30) Foreign Application Priority Data

Nov. 19, 2019 (JP) ................................. 2019-208890

(51) Int. Cl.
*G01N 33/543* (2006.01)
*G01N 21/51* (2006.01)
*G01N 21/59* (2006.01)

(52) U.S. Cl.
CPC ....... *G01N 33/54373* (2013.01); *G01N 21/51* (2013.01); *G01N 21/59* (2013.01)

(58) Field of Classification Search
CPC ......... G01N 2021/0357; G01N 21/253; G01N 21/51; G01N 21/59; G01N 21/78;
(Continued)

(56) References Cited

U.S. PATENT DOCUMENTS

| 5,073,029 A | 12/1991 | Eberly et al. |
| 5,216,488 A | 6/1993 | Tuunanen et al. |

(Continued)

FOREIGN PATENT DOCUMENTS

| EP | 2 407 788 A1 | 1/2012 |
| EP | 3 382 398 A1 | 10/2018 |

(Continued)

OTHER PUBLICATIONS

Extended European Search Report for corresponding European Application No. 20889859.3, dated Dec. 14, 2022.
(Continued)

*Primary Examiner* — Tri T Ton
(74) *Attorney, Agent, or Firm* — Birch, Stewart, Kolasch & Birch, LLP

(57) ABSTRACT

A test device includes a specimen having a circular cross section that accommodates a test target, a specimen holding part that holds a plurality of the specimens in a row, light emitting elements in which light is incident on two adjacent specimens among the plurality of specimens, a first light guide path 46 that guides light emitted by the light emitting elements, and a second light guide path that is formed to have a smaller diameter than a diameter of the first light guide path and that guides the light emitted by the light emitting elements from the first light guide path to the specimen.

17 Claims, 5 Drawing Sheets

(58) Field of Classification Search
CPC .......... G01N 21/82; G01N 2201/0407; G01N 2201/064; G01N 33/54373; G01N 33/579; C12M 1/34
USPC .......................................................... 356/337
See application file for complete search history.

(56) References Cited

U.S. PATENT DOCUMENTS

| | | |
|---|---|---|
| 2012/0100624 A1 | 4/2012 | Hara et al. |
| 2013/0309704 A1* | 11/2013 | Inada ............... G01N 33/54393 435/23 |
| 2014/0011266 A1* | 1/2014 | Webster .................... B01L 7/52 435/303.1 |
| 2014/0322819 A1 | 10/2014 | Witte et al. |
| 2018/0003732 A1 | 1/2018 | Fujiwara et al. |
| 2018/0252646 A1 | 9/2018 | Ying et al. |
| 2019/0113514 A1 | 4/2019 | Ye et al. |
| 2021/0055223 A1 | 2/2021 | Nazirizadeh et al. |

FOREIGN PATENT DOCUMENTS

| | | |
|---|---|---|
| FR | 2 668 597 A1 | 4/1992 |
| JP | 9-159671 A | 6/1997 |
| JP | 3268462 B2 | 3/2002 |
| JP | 2011-2379 A | 1/2011 |
| JP | 2012-154815 A | 8/2012 |
| JP | 2013-528359 A | 7/2013 |
| JP | 2014-215298 A | 11/2014 |
| JP | 2018-9953 A | 1/2018 |
| WO | WO 2019/214971 A1 | 11/2019 |

OTHER PUBLICATIONS

Zhang et al., "The Current Status and Development of OD Measurement Technique," Proc. of SPIE, IEEE, vol. 9046, 2013, pp. 904614-1-904614-7.

Japanese Office Action for corresponding Japanese Application No. 2021-558220, dated Apr. 25, 2023, with English translation.

International Preliminary Report on Patentability and English translation of the Written Opinion of the International Searching Authority (Forms PCT/IB/326, PCT/IB/373 and PCT/ISA/237) for International Application No. PCT/JP2020/038808, dated Jun. 2, 2022.

International Search Report (Form PCT/ISA/210) for International Application No. PCT/JP2020/038808, dated Dec. 22, 2020, with English translation.

* cited by examiner

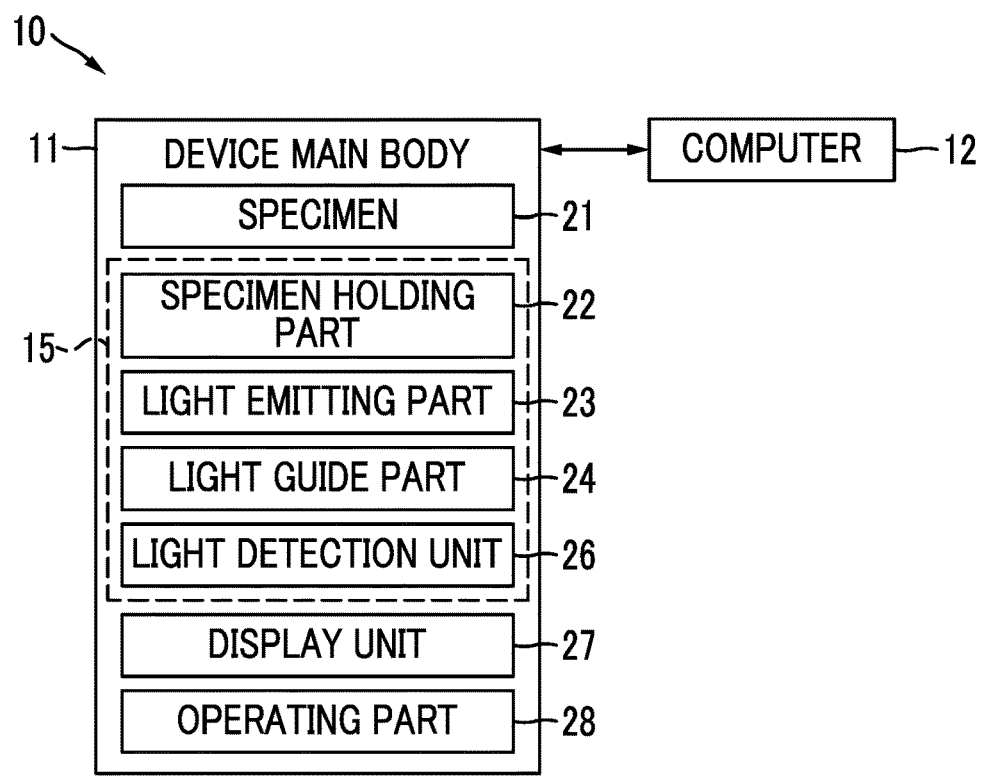
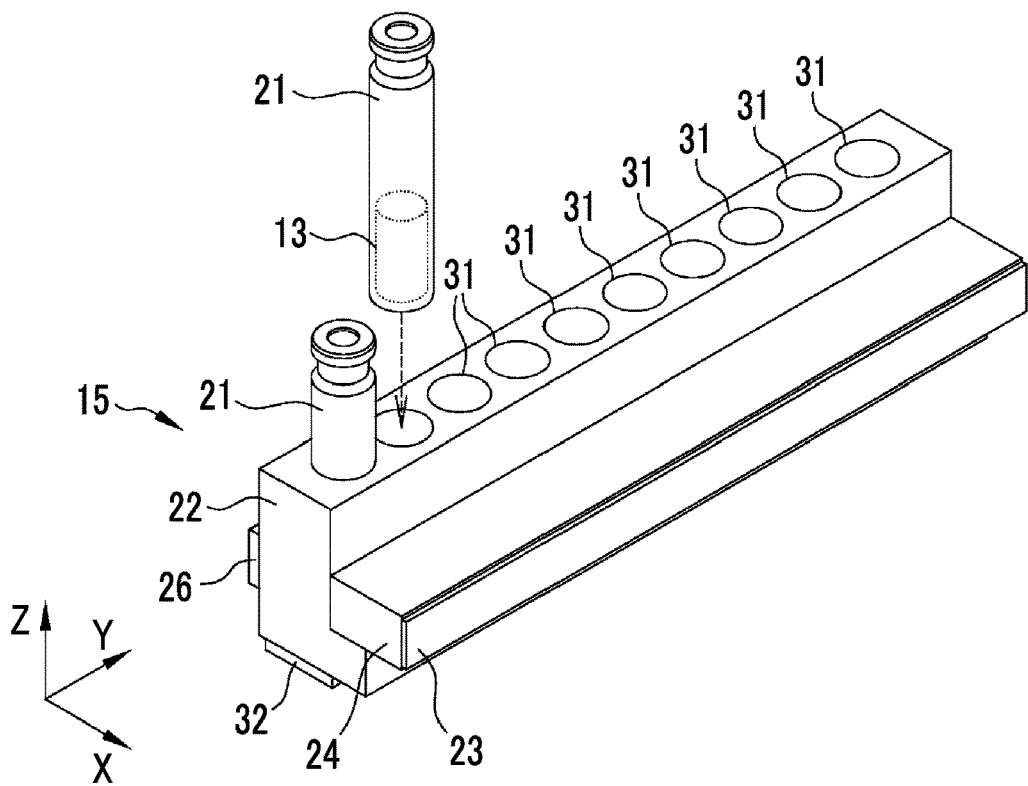

TEST DEVICE

CROSS-REFERENCE TO RELATED APPLICATIONS

This application is a Continuation of PCT International Application No. PCT/JP2020/038808 filed on Oct. 14, 2020, which claims priority under 35 U.S.C § 119(a) to Japanese Patent Application No. 2019-208890 filed on Nov. 19, 2019. Each of the above application(s) is hereby expressly incorporated by reference, in its entirety, into the present application.

BACKGROUND OF THE INVENTION

1. Field of the Invention

The present invention relates to a test device that tests a sample using light.

2. Description of the Related Art

Endotoxin present on a cell wall of a Gram-negative bacteria causes various biological reactions such as fever in a case where endotoxin is mixed in blood even in a trace amount of approximately nanogram to picogram. In addition, endotoxin has high heat resistance, and even in a case where Gram-negative bacteria are killed by an autoclaving treatment, it is difficult to inactivate endotoxin. Therefore, it is necessary to perform a test to confirm that endotoxin is not contaminated with a drug such as an injection and a medical device in Which endotoxin may be mixed in the blood. In addition, in a case where humans or animals are infected with. Gram-negative bacteria, endotoxin is produced in the body and endotoxin stays in the blood. There is also a use for selecting a treatment method by collecting blood or body fluid from such a person or animal and testing for the presence or absence of endotoxin.

An endotoxin test is performed using a lysate reagent (so-called Limulus reagent) prepared from a horseshoe crab blood cell extract by utilizing the property of aggregating horseshoe crab blood cell extract. In addition, a test device for testing endotoxin is known (JP1997-159671A (JP-H9-159671A), JP2014-215298A, and JP2011-002379A). The lysate reagent prepared from horseshoe crab blood cell extract can also be used for measuring $(1\to3)$-$\beta$-D-glucan present on the cell wall of fungi, depending on the adjustment of the reagent components.

SUMMARY OF THE INVENTION

A test device for performing an endotoxin test (in addition to a test for measuring endotoxin, a test for measuring $(1\to3)$-$\beta$-D-glucan is also included. The same is applied hereinafter) disposes a plurality of specimens and performs these specimens sequentially or simultaneously. In addition to a gelation method, endotoxin test methods include a colorimetric method and a turbidimetric method. Therefore, the endotoxin test is performed by selecting from each of these test methods or combining these methods according to the characteristics of a sample held by each specimen. In addition, regarding the colorimetric method, in order to appropriately select a wavelength of light used for the test, the test device for performing the endotoxin test may be provided with a plurality of light emitting elements in advance.

As described above, in order to enable endotoxin test by a plurality of test methods for a plurality of specimens, it is necessary to provide the plurality of light emitting elements having different luminescence wavelengths for one specimen. Therefore, there is a problem that a size of the test device increases. In addition, an optical component for guiding the light emitted by the light emitting element to the specimen is a factor in increasing the size of the test device, but in a case where such an optical component is simplified, another problem may arise that test accuracy is reduced.

An object of the present invention is to provide a test device that holds a plurality of specimens, is compact in size, and can accurately perform an endotoxin or $(1\to3)$-$\beta$-D-glucan test by a plurality of test methods.

A test device according to an aspect of the present invention comprises a specimen having a circular cross section that accommodates a test target, a specimen holding part that holds a plurality of the specimens in a row, a light emitting element in which light is incident on two adjacent specimens among the plurality of specimens held in the specimen holding part, a first light guide path that guides light emitted by the light emitting element, and a second light guide path that is formed thinner than the first light guide path and that guides the light emitted by the light emitting element from the first light guide path to the specimen.

It is preferable that the first light guide path is provided in common to a plurality of the light emitting elements.

It is preferable that the second light guide path includes a through-hole parallel to a direction connecting the light emitting element and the specimen.

It is preferable that in the second light guide path, a plurality of plates having through-holes are disposed so as to transmit light parallel to a direction connecting the light emitting element and the specimen and orthogonal in an arrangement direction of specimen in the specimen holding part.

It is preferable that the device further comprises a light-receiving element that receives light transmitted or scattered by the specimen for each specimen.

It is preferable that in the light emitting element, light is incident from an oblique direction with respect to a direction connecting the light-receiving element and the specimen.

It is preferable that the light-receiving element includes a shielding member that limits incidence of light, and receives light transmitted or scattered by the specimen through an opening of the shielding member.

It is preferable that the opening has a shape long in an arrangement direction of the light emitting elements.

It is preferable that the opening includes a color filter that selectively transmits light emitted by the light emitting element.

It is preferable that the opening is divided into a plurality of regions, and includes the color filter in which a color of the transmitted light is different for each region.

It is preferable that the light emitting elements includes a first color light emitting element that emits light of a first color, and a second color light emitting element that emits light of a second color different from the first color, and the first color light emitting element and the second color light emitting element are alternately arranged in an arrangement of the plurality of light emitting elements.

It is preferable that the device further comprises a third color light emitting element that emits light of a third color different from the first color and the second color, and in which light is incident from a direction connecting the light-receiving element and the specimen and orthogonal in an arrangement direction of specimen in the specimen holding part, between the first color light emitting element and the second color light emitting element, in addition to the light emitting element.

A test device according to another aspect of the present invention comprises a plurality of measuring units that includes a specimen having a circular cross section which accommodates a test target, a specimen holding part which holds a plurality of the specimens in a row, a light emitting element in which light is incident on two adjacent specimens among the plurality of specimens, a first light guide path which guides light emitted by the light emitting element, and a second light guide path formed to have a smaller diameter than a diameter of the first light guide path and which guides the light emitted by the light emitting element from the first light guide path to the specimen.

The test device of the embodiment of the present invention holds the plurality of specimens, is compact in size, and can accurately perform the endotoxin or (1→3)-β-D-glucan test by the plurality of test methods.

BRIEF DESCRIPTION OF THE DRAWINGS

FIG. 1 is a block diagram showing a configuration of a test device.

FIG. 2 is a perspective view of a measuring unit and a specimen.

DESCRIPTION OF THE PREFERRED EMBODIMENTS

First Embodiment

Figure 3:
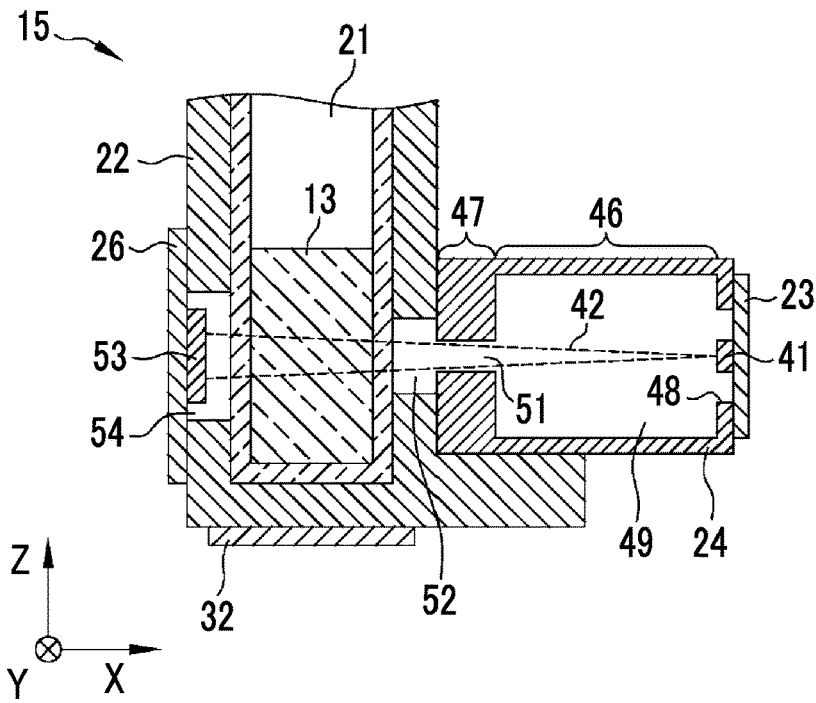
FIG. 3 is an XZ cross-sectional view of the measuring unit.

As shown in FIG. 1, a test device 10 is provided with a device main body 11 and a computer 12. The test device 10 tests a test target 13 (refer to FIG. 2) for the presence or absence of contamination by endotoxin by performing optical measurement, and measures the content or concentration of endotoxin if necessary. The test target 13 is a solution in which a lysate reagent and a tested object are mixed. For example; the tested object is an injection such as a vaccine or a blood preparation, water obtained by recovering endotoxin from the tested object such as a syringe or an injection needle, polyethylene glycol, ethylenediamine tetraacetic acid (so-called recovery liquid), or blood or body fluid collected from a patient who may be infected with Gram-negative bacteria or fungi, or the like. The lysate reagent is Limulus Amebocyte Lysate (LAL) or Tachypleus Amebocyte Lysate (TAL).

The lysate reagent prepared from horseshoe crab blood cell extract can also be used for measuring (1→3)-β-D-glucan present on the cell wall of fungi, depending on the adjustment of the reagent components. The lysate reagent is used in a test to determine the presence or absence of fungal infection by measuring the concentration of (1→3)-β-D-glucan in the patient's blood or body fluid. In the present specification, in a case of being described as endotoxin, endotoxin may be read as (1→3)-β-D-glucan, and the test device 10 for endotoxin test also functions as a (1→3)-β-D-glucan test device. In addition, one test device 10 can test both endotoxin and (1→3)-β-D-glucan.

The device main body 11 is a portion of the test device 10 including a measuring unit 15 for performing optical measurement of a sample. Specifically, the device main body 11 is provided with a specimen 21, a specimen holding part 22, a light emitting part 23, a light guide part 24, a light detection unit 26, a display unit 27, an operating part 28, and the like. Of these, the specimen holding part 22, the light emitting part 23, the light guide part 24, and the light detection unit 26 constitute the measuring unit 15.

The specimen 21 is a container having a circular cross section for accommodating the test target 13. In the present embodiment, a state where the test target is accommodated is also simply referred to as the specimen 21. The circular cross section means that the outer shape of the cross section is a circle, an ellipse, or a substantially smooth closed curve similar thereto in a case where at least a portion accommodating the test target 13 (especially a portion irradiated with light for test) is cut horizontally, in the state of being disposed in the device main body 11. In the present embodiment, as shown in FIG. 2, the specimen 21 is substantially cylindrical. In addition, the specimen 21 is made of heat-resistant glass. This is to prevent the specimen 21 before accommodating the test target from containing endotoxin and (1→3)-β-D-glucan, for example, by the dry heat sterilization treatment at 250° C. or higher and 30 minutes or longer.

The specimen holding part 22 holds a plurality of specimens 21 side by side. The specimen holding part 22 has a plurality of openings 31 arranged in a row (refer to FIG. 2). Therefore, by inserting the specimen 21 into each opening 31, the specimen holding part 22 holds the plurality of specimens 21 side by side in a row. In the present embodiment, the specimen holding part 22 has ten openings 31, and by inserting the specimen 21 into all of these openings, ten specimen 21 can be held at the same time. The specimen holding part 22 may hold 11 or more or 9 or less specimens 21. In addition, the specimen holding part 22 has a heater 32 on the bottom surface (surface on the negative side in the Z direction). By controlling the on and off of the heater 32, the temperature of the specimen holding part 22 and the specimen 21 held by the specimen holding part 22 can be maintained within a predetermined temperature or a predetermined temperature range. Therefore, the specimen holding part 22 also functions as a so-called constant-temperature tank.

The light emitting part 23 irradiates the specimen 21 held by the specimen holding part 22 with light used for test. As shown in FIG. 3, the light emitting part 23 is provided with a light emitting element 41. The light emitting element 41 is, for example, a light emitting diode (LED), and by emitting light, light 42 used for test is incident on the specimen 21. In addition, the light emitting element 41 emits light in a wide range such that at least two or more specimens 21 can be irradiated with the light 42. Since the light emitting element 41 sends light 42 to a plurality of measurement sites (the plurality of specimens 21), it is desirable that the light emitting element 41 is a diffusion light source in which each measurement site (each specimen 21) can obtain substantially the same amount of light in a certain direction.

The light guide part 24 guides the light 42 emitted by the light emitting element 41 to the specimen 21 held by the specimen holding part 22. Specifically, the light guide part 24 includes a first light guide path 46 and a second light guide path 47 (refer to FIG. 3).

The first light guide path 46 is a portion of the light guide part 24 that is relatively located on the light emitting element 41 side, and includes an opening 48 at a connection portion with the light emitting part 23. In a case where the light emitting part 23 is connected to the light guide part 24, the light emitting element 41 is exposed to the first light guide path 46 through the opening 48. Therefore, the first light guide path 46 is a space that directly receives the light 42 generated by the light emitting element 41 and propagates the light 42 to the second light guide path 47. In the present embodiment, the first light guide path 46 is a space 49 filled with air and capable of being ventilated to the outside. However, a part or all of the space 49 may be filled with a dielectric material or the like, if necessary. The first light guide path 46 is for guiding the light 42 generated by the light emitting element 41 that emits light in a wide range toward at least two or more specimens 21 adjacent to each other.

The second light guide path 47 is formed to have a relatively smaller diameter than that of the first light guide path 46, and guides the light 42 emitted by the light emitting element 41 from the first light guide path 46 to the specimen 21. Specifically, the second light guide path 47 is a portion of the light guide part 24 that is relatively located on the specimen holding part 22 side, and includes a through-hole 51 at a connection portion with the specimen holding part 22. The through-hole 51 is a through-hole parallel to the direction connecting the light emitting element 41 and the specimen 21. In addition, the specimen holding part 22 is provided with an opening 52 at a position where at least the through-hole 51 of the second light guide path 47 is exposed to the specimen 21. Therefore, of the light 42 propagating in the space 49 of the first light guide path 46, the light 42 incident on the through-hole 51 of the second light guide path 47 is incident on the specimen 21 through the opening 52.

The fact that "the diameter is relatively small with respect to the first light guide path 46" means that the diameter (cross-sectional area in the YZ direction) of the through-hole 51 of the second light guide path 47 is smaller than the diameter (cross-sectional area in the YZ direction) of the space 49 of the first light guide path 46 at a connection portion between the through-hole 51 and the space 49. In addition, the through-hole 51 of the second light guide path 47 is longer than the effective diameter of the opening (incident port of the light 42) on the space 49 side in the X direction. That is, the through-hole 51 has a substantial thickness in the XY in-plane direction, not just a surface. As a result, the second light guide path 47 limits an incidence angle of the light 42 from the space 49 side to the through-hole 51 and an emission angle of the light 42 from the through-hole 51 on the specimen 21 side. As a result, the second light guide path 47 prevent the light 42 reflected or the like in the space 49 from being incident on the through-hole 51 at a wide angle, and prevents such light 42 from being emitted from the through-hole 51 at a wide angle and incident on the specimen 21. In addition, the second light guide path 47 suppresses incident light from a light emitting element different from the light emitting element 41 that emits light in a wide range facing the second light guide path 47 from passing through the second light guide path 47, and suppresses the generation of a false signal due to the reflected light that may occur in a case of passing through incident on the specimen 21. That is, in the second light guide path 47, the light 42 incident on the specimen 21 is the light from only the facing light emitting element 41, and the light 42 is limited to substantially parallel light, in addition, the fact that the through-hole 51 is provided at a position away from the light emitting element 41 via the space 49 also contributes to making the light 42 incident on the specimen 21 substantially parallel light. Substantially parallel light means light that maintains parallelism to the extent that the light passes directly through the through-hole from the light emitting element.

The light detection unit 26 is provided with a light-receiving element 53 that receives the light transmitted or scattered by the specimen 21. The light-receiving element 53 is, for example, an optical sensor such as a photo diode (PD), and is provided for each specimen 21, In the present embodiment, since the specimen holding part 22 holds ten specimens 21, the light detection unit 26 is provided with the light-receiving element 53 at a position where the light 42 transmitted through each of these specimens 21 can be received. In addition, the specimen holding part 22 is provided with an opening 54 between the specimen 21 and the light-receiving element 53 having a range in which at least the light-receiving element 53 is exposed to the specimen 21 side. Therefore, the light 42 transmitted through the specimen 21 reaches the light-receiving element 53 through the opening 54.

Figure 4:
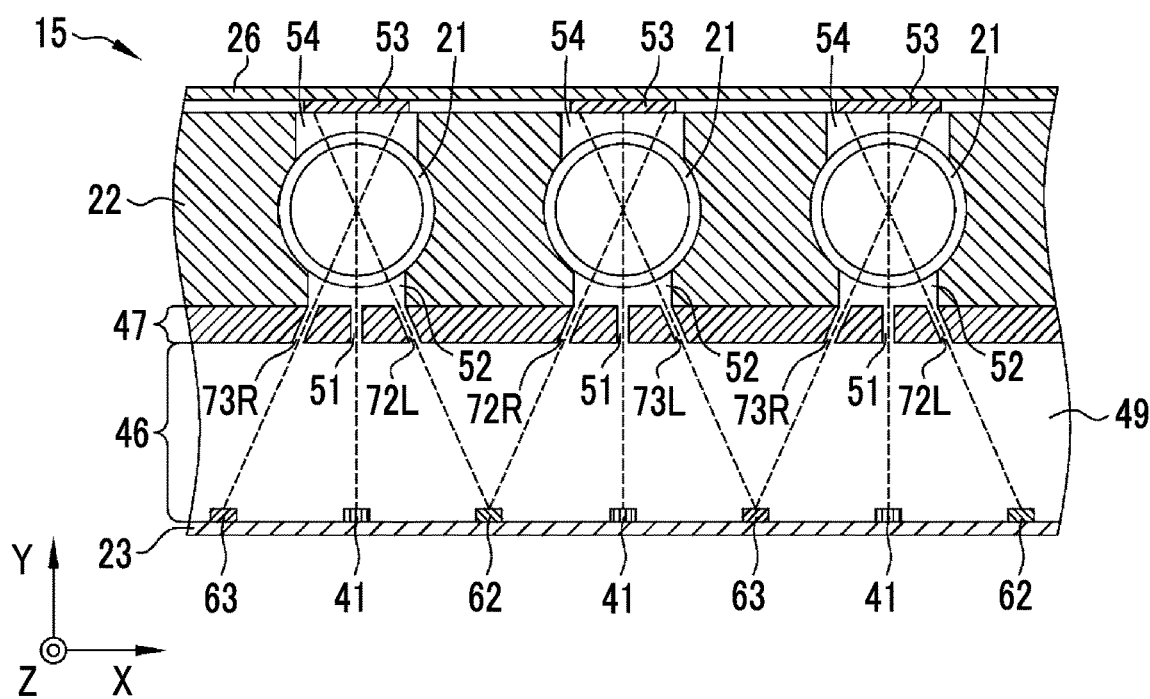
FIG. 4 is an XY cross-sectional view of the measuring unit.

As shown in FIG. 4, the light emitting part 23 is provided with a light emitting element 62 and a light emitting element 63 that emit light in a wavelength band different from that of the light emitting element 41, in addition to the light emitting element 41. The light emitting element 62 and the light emitting element 63 emit light in a wide range to the extent that light can be irradiated toward at least two or more specimens 21, As described above, since the light emitting element 62 and the light emitting element 63 send light to a plurality of measurement sites (the plurality of specimens 21), it is desirable that the light emitting element 62 and the light emitting element 63 are diffusion light sources in which each measurement site (each specimen 21) can obtain substantially the same amount of light in a certain direction. In addition, a plurality of each of the light emitting element 41, the light emitting element 62, and the light emitting element 63 are provided, and the light emitting element 41, the light emitting element 62, and the light emitting element 63 are periodically disposed in this order along the X direction.

The light emitting element 41 is disposed substantially in front of each of the light-receiving element 53 and the specimen 21, and in the endotoxin test, the light emitting element 41 irradiates the specimen 21 in front of the light emitting element 41 with light 42 through the space 49 of the first light guide path 46 and the through-hole 51 of the second light guide path 47. The light emitting element 41 is used, for example, in a case of testing by a turbidimetric method, and the light 42 emitted by the light emitting element 41 is, for example, red. The front surface refers to a position on an extension of the normal of the light-receiving surface of the light-receiving element 53 passing through the center of the specimen 21.

The light emitted by the light emitting element 62 is, for example, purple. In addition, the light emitted by the light emitting element 63 is, for example, blue. The light emitting element 62 and the light emitting element 63 are selected and used, for example, in a case of testing by a colorimetric method. In addition, focusing on the arrangement of the light emitting element 62 and the light emitting element 63 in the arrangement of the plurality of light emitting elements, these elements are arranged alternately in the X direction. That is, the measuring unit 15 is provided with the light emitting element 62, which is a first color light emitting element that emits light of a first color (for example, purple), and the light emitting element 63, which is a second color light emitting element that emits light of a second color (for example, blue) different from that of the first color, as the light emitting element. In the arrangement of the plurality of light emitting elements, the light emitting element 62 which is the first color light emitting element and the light emitting element 63 which is the second color light emitting element are arranged alternately. As a result, light can be incident on any of the plurality of specimens 21 held by the specimen holding part 22 from each of the light emitting element 62 and the light emitting element 63.

In a case where the light emitting element 62 and the light emitting element 63 are the first color light emitting element and the second color light emitting element as described above, the light emitting element 41 is a third color light emitting element. That is, the measuring unit 15 is provided with a light emitting element 41 which is the third color light emitting element that emits light of a third color (for example, red) different from the first color and the second color (for example, purple and blue) and on which light is incident from the direction connecting the light-receiving element 53 and the specimen 21 (in FIG. 4, the direction of the broken line passing through the center of the specimen 21 and connecting the light-receiving element 53 and the light emitting element 41), between the light emitting element 62 which is the first color light emitting element and the light emitting element 63 which is the second color light emitting element.

The light emitting element 62 and the light emitting element 63 are disposed at positions other than the front surface of the light-receiving element 53 and the specimen 21 (between the two light emitting elements 41 (particularly, intermediate point)). In addition, in a case where the light emitting element 62 and the light emitting element 63 each emit light, the light is simultaneously incident on two adjacent specimens 21 among the plurality of specimens 21 held by the specimen holding part 22. Therefore, light is incident on the light emitting element 62 and the light emitting element 63 from an oblique direction with respect to the direction connecting the light-receiving element 53 and the specimen 21.

For the above-described usage aspect, the first light guide path 46 is provided in common to a plurality of light emitting elements (the light emitting element 41, the light emitting element 62, and the light emitting element 63, each of which includes a plurality of light emitting elements). That is, the space 49 forming the first light guide path 46 is not divided for each specimen 21 or the like, and is a continuous region in the X direction. Therefore, the first light guide path 46 does not hinder the propagation of the light emitted by any light emitting element of the light emitting element 41, the light emitting element 62, and the light emitting element 63, each of which includes a plurality of light emitting elements.

In addition, in the second light guide path 47 includes a through-hole 72L, a through-hole 72R, a through-hole 73L, and a through-hole 73R that guide the light emitted by the light emitting element 62 and the light emitting element 63, in addition to the through-hole 51 that guides the light 42 emitted by the light emitting element 41.

The through-hole 72L and the through-hole 72R are through-holes parallel to the direction connecting the light emitting element 62 and the specimen 21. Therefore, the through-hole 72L guides the light emitted by the light emitting element 62 to the specimen 21 on the left side (negative side in the X direction) in a case of viewed from the light emitting element 62. The through-hole 72R guides the light emitted by the light emitting element 62 to the specimen 21 on the right side (positive side in the X direction) in a case of viewed from the light emitting element 62.

Similarly, the through-hole 73L and the through-hole 73R are through-holes substantially parallel to the direction connecting the light emitting element 63 and the specimen 21. Therefore, the through-hole 73L guides the light emitted by the light emitting element 63 to the specimen 21 on the left side (negative side in the X direction) in a case of viewed from the light emitting element 63. The through-hole 73R guides the light emitted by the light emitting element 63 to the specimen 21 on the right side (positive side in the X direction) in a case of viewed from the light emitting element 63.

In the through-hole 72L, the through-hole 72R, the through-hole 73L, and the through-hole 73R, the diameter of each of the through-hole 72L, the through-hole 72R, the through-hole 73L, and the through-hole 73R. (cross-sectional area in the YZ direction) is smaller than the diameter of the first light guide path 46 (cross-sectional area in the YZ direction), at the connection portion with the space 49. Therefore, regarding the through-hole 72L, the through-hole 72R, the through-hole 73L, and the through-hole 73R, the second light guide path 47 is formed to have a relatively smaller diameter than that of the first light guide path 46, and guides the light emitted by the light emitting element 62 and the light emitting element 63 from the first light guide path 46 to the specimen 21. The opening 52 of the specimen holding part 22 exposes the through-hole 72L, the through-hole 72R, the through-hole 731L, and the through-hole 73R to the specimen 21. In addition, the opening 54 of the specimen holding part 22 does not prevent the light incident on the specimen 21 from reaching the light-receiving element 53 through the through-hole 72L, the through-hole 72R, the through-hole 73L, and the through-hole 73R.

In addition, the through-hole 72l, the through-hole 72R, the through-hole 73L, and the through-hole 73R are longer in the extending direction than the effective diameter of the opening (light incident port) on the space 49 side, and these through-holes are not merely surfaces, but have substantial thickness. Therefore, the second light guide path 47 prevents light reflected or the like in the space 49 from entering the through-hole 72l, the through-hole 72R, the through-hole 73L, and the through-hole 73R at a wide angle, and prevents such light from being emitted from the through-hole 72L, the through-hole 72R, the through-hole 73L, and the through-hole 73R at a wide angle and incident on the specimen 21. That is, even in a case where the light emitting element 62 and the light emitting element 63 are used, the second light guide path 47 limits the light incident on the specimen 21 to substantially parallel light. In addition, the fact that the through-hole 72L, the through-hole 72R, the through-hole 73L, and the through-hole 73R are provided at positions away from the light emitting element 62 and the light emitting element 63 via the space 49 also contributes to making the light 42 incident on the specimen substantially parallel light.

The display unit 27 is, for example, an indicator indicating whether or not the test can be executed and/or the progress of the test. In addition, the display unit 27 can be a display screen such as a liquid crystal panel, or a touch panel, and the like.

The operating part 28 is a switch or the like for directly giving an operation instruction to the device main body 11. In a case where the display unit 27 is a touch panel, at least a part of the operating part 28 can be formed by using a graphical user interface displayed on the touch panel.

The computer 12 is a part of the test device 10 that controls each part of the device main body 11 and performs analysis or determination using measurement data (signals and the like acquired from the light-receiving element 53) acquired from the device main body 11. Specifically, the computer 12 acquires the measurement data from the measuring unit 15 and analyzes or the like using the measurement data to determine the presence or absence of endotoxin or to generate data that can determine the presence or absence of endotoxin. In the present embodiment, the computer 12 is provided separately from the device main body 11, but a part or all of the functions of the computer 12 can be incorporated into the device main body 11.

In the test device 10, endotoxin test by a colorimetric method and a turbidimetric method can be performed. The colorimetric method is a test method of identifying the presence or absence of endotoxin by measuring the activation of the lysate reagent by endotoxin by the absorbance at a specific wavelength. Since the measuring unit 15 is provided with two types of light emitting elements of the light emitting element 62 and the light emitting element 63 for test by the colorimetric method, the measuring unit 15 performs an endotoxin test using either the light emitting element 62 or the light emitting element 63 according to the characteristics of the test target 13. The turbidimetric method is a test method of identifying the presence or absence of endotoxin by measuring the change in turbidity of a sample gelled by activation of a lysate reagent by endotoxin in the test by the turbidimetric method, the light emitting element 41 for each specimen 21 is used.

As described above, the test device 10 is provided with three types of light emitting elements of the light emitting element 41, the light emitting element 62, and the light emitting element 63, for endotoxin test by the turbidimetric method and the colorimetric method. The light emitting element 62 and the light emitting element 63 for the colorimetric method are disposed between two adjacent specimens 21, and light is incident on both of the two adjacent specimens 21 from one of the light emitting element 62 or the light emitting element 63. Therefore, the length in the X direction can be shortened for one specimen 21 as compared with the case where the light emitting element 41, the light emitting element 62, and the light emitting element 63 are provided one by one, and the size of the test device 10 as a whole can be reduced. In addition, as in the first embodiment, the compact size can be maintained even in a case where the light emitting element 41 for the turbidimetric method is added to each specimen 21.

In addition, since the specimen 21 is made of glass to withstand the city heat sterilization treatment and has a circular cross section, in a case where light is incident on the specimen 21 from an oblique direction, the light may be reflected on the surface of the specimen 21 to cause the light to be unlikely to be incident on the test target 13, and as a result, the teat accuracy may decrease. For example, in a case where the light used for test is guided by an optical fiber or the like, or in a case where the light is focused on the specimen 21 through a stop having substantially no thickness, the amount of light expected to be incident on the specimen 21 and the test target 13 is different from the amount of light actually incident on the specimen 21 and the test target 13 due to a slight displacement of the position of the specimen 21 or the like, and as a result, the test accuracy may decrease. However, in the test device 10, by guiding light to the specimen 21 by the first light guide path 46 and the second light guide path 47, the light emitted by the light emitting element 62 or the light emitting element 63 can be incident on both of the two adjacent specimens 21. On the other hand, the light incident on the specimen 21 is narrowed down by the through-hole (through-hole 72L or the like) and is arranged to be substantially parallel light. Therefore, as compared with the case of using the above-described optical fiber, stop, or the like, it is easier to cause the planned amount of light to be incident on the specimen 21 and the test target 13. As a result, the test device 10 can hold the plurality of specimens 21 and can accurately perform the endotoxin test by the plurality of test methods while being formed into a compact size.

Furthermore, as described above, in the test device 10, since the light incident on the specimen 21 is narrowed down by the through-hole (through-hole 72L or the like) and is arranged to be substantially parallel light, depending on the characteristics of the test target 13, such as containing a fat component, even in a case where the test target 13 is turbid from the beginning (before the reaction between endotoxin and lysate reagent), the light with the planned amount of light is likely to be incident on the test target 13. Therefore, the test device 10 can perform the endotoxin test with high accuracy.

In the first embodiment, it is desirable that the first light guide path 46 (that is, the inner surface forming the space 49 and the portion of the light emitting part 23 other than the light emitting element 41) and the second light guide path 47 (at least the surface (inner surface portion) forming the second light guide path 47) has as low reflection as possible. Therefore, it is preferable to form the first light guide path 46 and the second light guide path 47 by using a light-absorbing material, a surface coating, or the like. Therefore, the first light guide path 46 and the second light guide path 47 can be, for example, subjected to a matte black alumite treatment or coated with a black paint.

Figure 5:
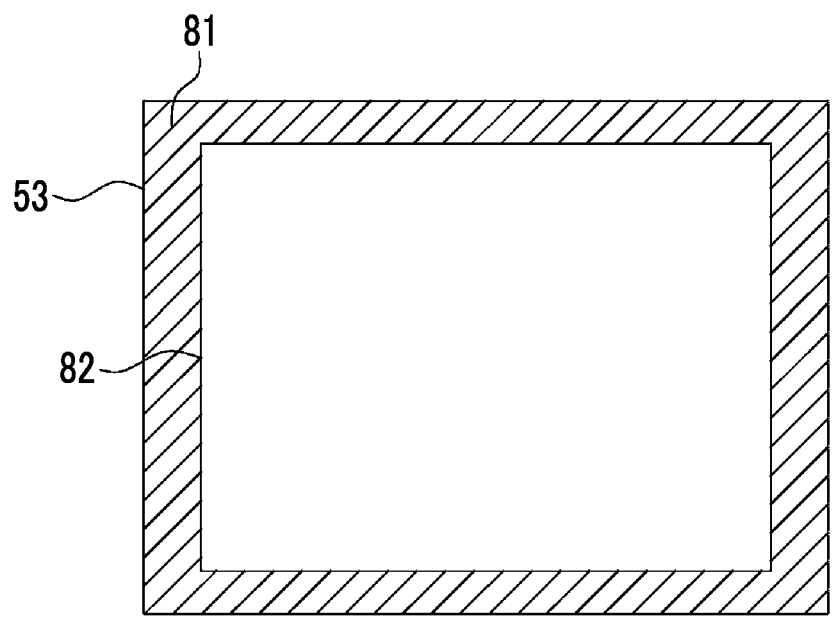
FIG. 5 is an explanatory diagram showing a configuration of a shielding member provided on a light-receiving surface of a light-receiving element.
Figure 6:
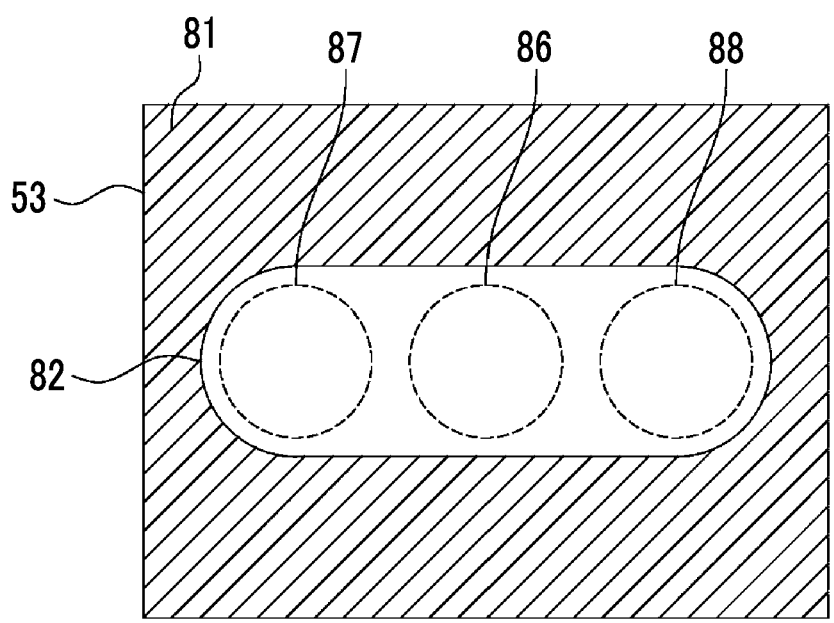
FIG. 6 is an explanatory diagram showing a configuration of another shielding member.

As shown in FIG. 5, it is preferable that the light-receiving element 53 mounted on the test device 10 of the first embodiment is provided with a shielding member 81 for limiting the incident light on the light-receiving surface thereof, and the specimen 21 receives light transmitted or scattered through an opening 82 of the shielding member 81. This is to limit the light-receiving of unintended stray light and scattered light and improve the test accuracy. In addition, it is preferable that the opening 82 provided in the shielding member 81 is formed to the minimum according to the position, size, and shape of the spot of light incident on the specimen 21 by the light emitting element 41, the light emitting element 62, and the light emitting element 63, For example, as shown in FIG. 6, it is preferable that the opening 82 is a so-called stadium type, and the shape is long in the arrangement direction (X direction) of the light emitting element 41, the light emitting element 62, and the light emitting element 63 so as to include a spot 86 reached by the light 42 emitted by the light emitting element 41, a spot 87 reached by the light emitted by the light emitting element 62, and a spot 88 reached by the light emitted by the light emitting element 63 to substantially the minimum. In this case, the light-receiving of unnecessary light can be limited to higher accuracy, and the test accuracy can be further improved. In addition to the stadium type, the shape long in the arrangement direction of the light emitting elements includes an ellipse or a rectangle having a major axis in the arrangement direction of the light emitting elements.

Figure 7:
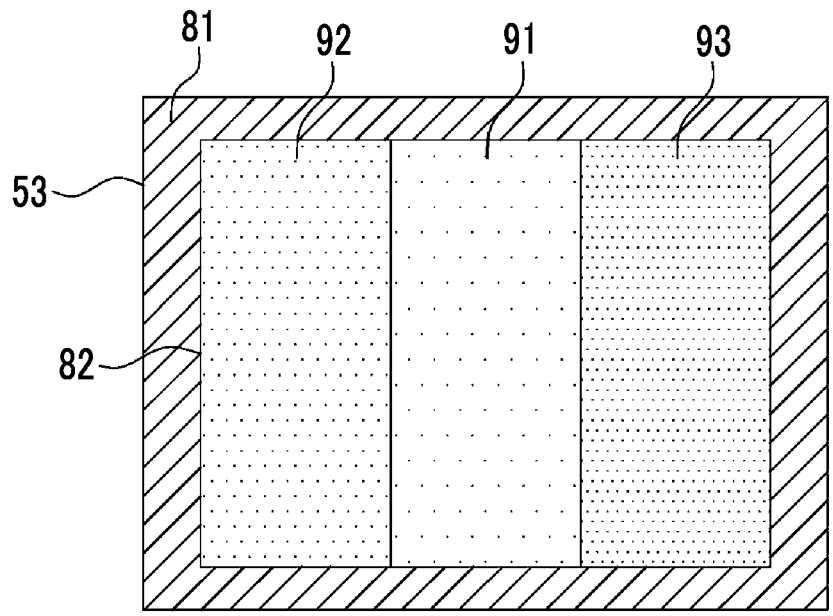
FIG. 7 is an explanatory diagram showing an example in which color filters are provided on the light-receiving surface of the light-receiving element.

As described above, in a case where the shielding member 81 having the opening 82 is used for the light-receiving element 53, it is preferable that the opening 82 is provided with a color filter that selectively transmits the light emitted by the light emitting element. In particular, it is preferable that the opening 82 is divided into a plurality of regions according to the positions, sizes, and shapes of the spots of light incident on the specimen 21 by the light emitting element 41, the light emitting element 62, and the light emitting element 63, and each region is provided with a color filter in which the color of the transmitted light is different. Specifically, as shown in FIG. 7, it is preferable to include color filters 91 to 93 that selectively transmit the light emitted by the light emitting element 41, the light emitting element 62, and the light emitting element 63. The color filter 91 selectively transmits the light 42 emitted by the light emitting element 41. The color filter 92 selectively transmits the light emitted by the light emitting element 62 (for example, purple light). The color filter 93 selectively transmits the light emitted by the light emitting element 63 (for example, blue light). By providing the color filters 91 to 93 in the opening 82 in this manner, test can be performed with higher accuracy. For example, in a case where the light emitting element 41 is used, this is because the size of the opening 82 is substantially limited to a certain portion of the color filter 91, which makes it difficult to receive the scattered light reaching the positions of the color filter 92 and the color filter 93. The same applies in a case where the light emitting element 62 or the light emitting element 63 is used.

Figure 8:
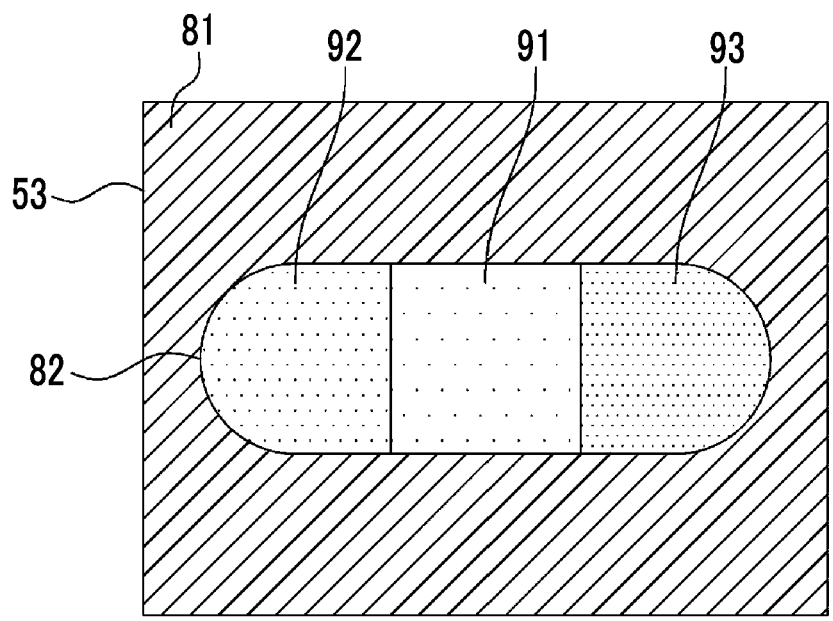
FIG. 8 is an explanatory diagram showing an example in which color filters are provided on the light-receiving surface of the light-receiving element.

As shown in FIG. 8, even in a case where the opening 82 has a shape long in the arrangement direction of the light emitting element having other than the stadium type, the openings 82 can be provided with the color filters 91 to 93. In this case, the outer size of the opening 82 is originally narrowed down to a small size, and the effective opening size is optimized by the color filters 91 to 93, so that the test can be performed with particularly high accuracy.

In the above modification example, the color filters 91 to 93 are used in the opening 82 of the shielding member 81, but the color filters 91 to 93 are extended to the end portion of the light-receiving surface of the light-receiving element 53, so that the shielding member 81 can be omitted. In addition, the above modification example is an example in a case where one light-receiving element 53 is provided for each specimen 21, but the number of light-receiving elements 53 may be increased and two or three light-receiving elements may be provided for each specimen 21 according to the number of incidence wavelengths (type of light emitting element). In this case, the shielding member 81 may be appropriately provided for each of the light-receiving elements, and the color filters 91 to 93 may be provided to further improve the measurement accuracy.

Second Embodiment

In the first embodiment and the modification example, the second light guide path 47 having a substantial thickness in the XY in-plane direction is formed by providing the through-hole 51 or the like in one plate-shaped member, but the second light guide path 47 can be formed in another form. For example, the second light guide path 47 may have a configuration in which a plurality of plates having through-holes (hereinafter referred to as a through-hole plate) are disposed so that light penetrates in parallel to the direction connecting the light emitting element 41 or the like and the specimen 21.

Figure 9:
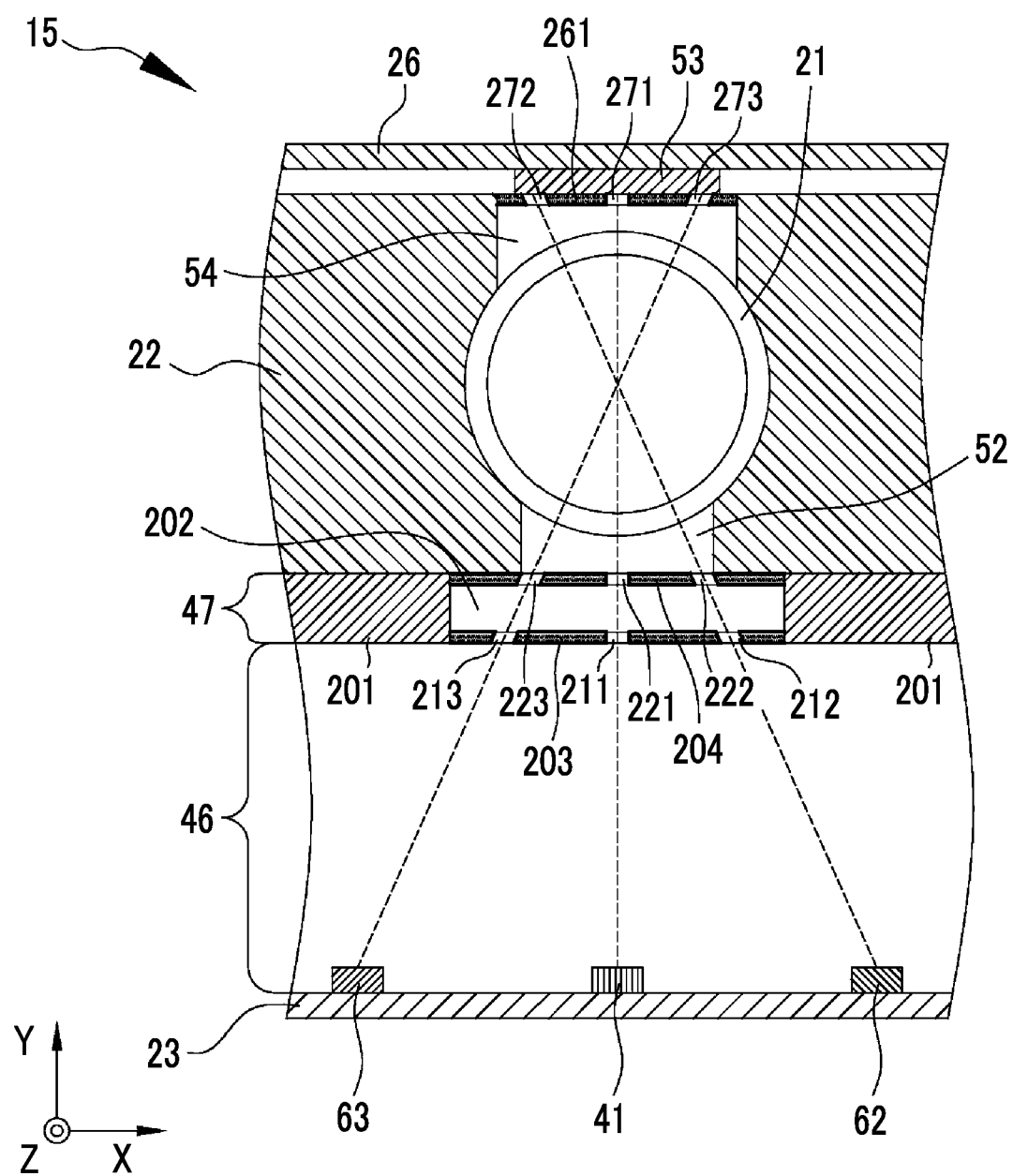
FIG. 9 is an XY cross-sectional view of a measuring unit according to a second embodiment.

Specifically, as shown in FIG. 9, a partition member 201 for partitioning the first light guide path 46 and the specimen holding part 22 is provided, and the partition member 201 is provided with an opening 202 in front of each specimen 21 for passing the light emitted by the light emitting element 41, the light emitting element 62, and the light emitting element 63 on the specimen 21 side. The opening 202 is provided with a first through-hole plate 203 and a second through-hole plate 204, respectively, in front of and behind the opening 202 (for example, opening ends on the light emitting element 41 side and the like and on the specimen 21 side).

The first through-hole plate 203 is provided on the front end side (the side of the light emitting element 41 or the like) of the opening 202, and includes a first through-hole 211, a second through-hole 212, and a third through-hole 213. The first through-hole 211 is on a straight line connecting the light emitting element 41 and the specimen 21, the second through-hole 212 is on the straight line connecting the light emitting element 62 and the specimen 21, and the third through-hole 213 is on the straight line connecting the light emitting element 63 and the specimen 21.

In addition, the second through-hole plate 204 is provided on the rear end side (side of the specimen 21) of the opening 202, and includes a first through-hole 221, a second through-hole 222, and a third through-hole 223. The first through-hole 221 is on a straight line connecting the light emitting element 41 and the specimen 21, the second through-hole 222 is on the straight line connecting the light emitting element 62 and the specimen 21, and the third through-hole 223 is on the straight line connecting the light emitting element 63 and the specimen 21.

In a case where the second light guide path 47 is formed by using the first through-hole plate 203 and the second through-hole plate 204 as described above, the first through-hole 211 of the first through-hole plate 203 and the first through-hole 221 of the second through-hole plate 204 function substantially in the same manner as the through-hole 51 of the first embodiment. That is, the first through-hole 211 of the first through-hole plate 203 and the first through-hole 221 of the second through-hole plate 204 limit the incidence angle of the light 42 emitted by the light emitting element 41 and the emission angle of the light 42 on the specimen 21 side. On the other hand, unlike the through-hole 51 of the first embodiment, since the space between the first through-hole 211 of the first through-hole plate 203 and the first through-hole 221 of the second through-hole plate 204 is hollow, only the light 42 that travels accurately and substantially straight and passes through between these through-holes reaches the specimen 21. In the case of the through-hole 51 of the first embodiment, although significantly minute amount of light reflected by the inner wall of the through-hole 51 may generate a false signal, as described above, the through-hole 51 of the first embodiment is formed by the first through-hole 211 of the first through-hole plate 203 and the first through-hole 221 of the second through-hole plate 204. Therefore, the incidence angle of the light 42 emitted by the light emitting element 41 and the emission angle of the light 42 on the specimen 21 side can be more accurately limited, and the generation of a false signal can be suppressed more reliably.

In addition, in a case where the second light guide path 47 is formed by using the first through-hole plate 203 and the second through-hole plate 204, the second through-hole 212 of the first through-hole plate 203 and the second through-hole 222 of the second through-hole plate 204 function substantially in the same manner as the through-hole 72L, (or through-hole 72R) of the first embodiment, and the incidence angle of the light emitted by the light emitting element 62 and the emission angle of the light on the specimen 21 side are limited. The limitation of the incidence angle and the emission angle is more accurate than that of the through-hole 72L, (or through-hole 72R) of the first embodiment, and the generation of a false signal can be suppressed more reliably.

Similarly, in a case where the second light guide path 47 is formed by using the first through-hole plate 203 and the second through-hole plate 204, the third through-hole 213 of the first through-hole plate 203 and the third through-hole 223 of the second through-hole plate 204 function substantially in the same manner as the through-hole 73L (or through-hole 73R) of the first embodiment, and the incidence angle of the light emitted by the light emitting element 63 and the emission angle of the light on the specimen 21 side are limited. The limitation of the incidence angle and the emission angle is more accurate than that of the through-hole 73L (or through-hole 73R) of the first embodiment, and the generation of a false signal can be suppressed more reliably.

In the second embodiment, the second light guide path 47 is formed by using two through-hole plates of the first through-hole plate 203 and the second through-hole plate 204, but the second light guide path 47 may be formed by using three or more through-hole plates by disposing through-hole plates similar to these through-hole plates between the first through-hole plate 203 and the second through-hole plate 204.

In addition, as in a third through-hole plate 261 (refer to FIG. 9), a through-hole plate similar to the first through-hole plate 203 and the second through-hole plate 204 described above can be provided in or at the end portion of the opening 54 having a range in which the light-receiving element 53 is exposed to the specimen 21 side. The third through-hole plate 261 includes a first through-hole 271, a second through-hole 272, and a third through-hole 273, The first through-hole 271 is on a straight line connecting the light emitting element 41 and the specimen 21, the second through-hole 272 is on the straight line connecting the light emitting element 62 and the specimen 21, and the third through-hole 273 is on the straight line connecting the light emitting element 63 and the specimen 21, in this manner, in a case where the third through-hole plate 261 is provided in the opening 54 provided on the front surface of the light-receiving element 53, the light scattered by the specimen 21 and/or the test target 13 or the like can be prevented from reaching the light-receiving element 53, and the generation of a false signal can be suppressed more reliably.

In FIG. 9, the first through-hole plate 203 includes the first through-hole 211, the second through-hole 212, and the third through-hole 213 opened along the traveling direction of light, and the second through-hole 212 and the third through-hole 213 are obliquely opened with respect to the first through-hole plate 203. However, the first through-hole 211, the second through-hole 212, and the third through-hole 213 (particularly the second through-hole 212 and the third through-hole 213) of the first through-hole plate 203 can be vertically opened with respect to the first through-hole plate 203. In this case, the first through-hole plate 203 is prefer- ably a thin plate within a range that does not interfere with measurement, strength, or the like. The same applies to the second through-hole plate 204 and the first through-hole 221, the second through-hole 222, and the third through-hole 223 thereof, and to the third through-hole plate 261 and the first through-hole 271, the second through-hole 272, and the third through-hole 273 thereof.

In addition, in FIG. 9, each of the first through-hole plate 203, the second through-hole plate 204, and the third through-hole plate 261 is provided independently for each specimen 21, but these through-hole plates may be provided in common to the plurality of specimens 21. That is, the plurality of first through-hole plates 203 can be integrally formed. The same applies to the second through-hole plate 204 and the third through-hole plate 261.

The second embodiment can be randomly combined with the first embodiment and the modification examples of the first embodiment for the configurations other than the second light guide path 47.

In the first embodiment, the second embodiment, and modification examples thereof, the test device 10 performs an endotoxin test by the turbidimetric method and the colorimetric method, but only in a case where only the test by the turbidimetric method is performed, the configuration (light emitting element 62, light emitting element 63, and the like) related to the test by the colorimetric method can be omitted. Similarly, in a case where the test device 10 only performs the test by the colorimetric method, the configuration (light emitting element 41, through-hole 51, and the like) related to the test by the turbidimetric method can be omitted. In addition, in a case where the test by the colorimetric method is performed with only one specific wavelength (for example, purple light or blue light), in the test device 10, either the light emitting element 62 and the configuration related thereto (through-hole 72L, through-hole 72R, and the like), or the light emitting element 63 and the configuration related thereto (through-hole 73L, through-hole 73R, and the like) can be omitted.

In the first embodiment, the second embodiment, and modification examples thereof, it is preferable that the light emitting element 62 and the light emitting element 63 are arranged at an intermediate point between the two light emitting elements 41. This is to allow light to be optically symmetrically incident on two adjacent specimens 21. In a case where light is optically symmetrically incident on two adjacent specimens 21, the test accuracy can be improved. It is particularly effective in a case where an operation is performed to determine the presence or absence of endotoxin.

In the first embodiment, the second embodiment, and modification examples thereof, the test device 10 performs an endotoxin test, but the present invention can be used for a device that performs a test other than the endotoxin test for detecting transmitted light, scattered light, or the like.

In the first embodiment, the second embodiment, and modification examples thereof, the test device 10 is provided with one measuring unit 15, but the test device 10 may be provided with a plurality of measuring units 15 in the device main body 11. That is, the test device 10 can be configured to include a plurality of measuring units 15 that include the specimen 21 having a circular cross section which accommodates the test target 13, the specimen holding part 22 which holds the plurality of specimens 21 in a row, the light emitting elements 62 and 63 in which light is incident on two adjacent specimens 21 among the plurality of specimens 21, the first light guide path 46 which guides light emitted by the light emitting element, and the second light guide path 47 formed to have a smaller diameter than a diameter of the first light guide path 46 and which guides the light emitted by the light emitting elements 62 and 63 from the first light guide path 46 to the specimen 21.

EXPLANATION OF REFERENCES

10: test device
11: device main body
12: computer
13: test target
15: measuring unit
21: specimen
22: specimen holding part
23: light emitting part
24: light guide part
26: light detection unit
27: display unit
28: operating part
31: opening
32: heater
41: light emitting element
42: light
46: first light guide path
47: second light guide path
48: opening
49: space
51: through-hole
52: opening
53: light-receiving element
54: opening
62: light emitting element
63: light emitting element
72L: through-hole
72R: through-hole
73L: through-hole
73R: through-hole
81: shielding member
82: opening
86: spot
87: spot
88: spot
91: color filter
92: color filter
93: color filter
201: partition member
202: opening
203: first through-hole plate
204: second through-hole plate
211: first through-hole
212: second through-hole
213: third through-hole
221: first through-hole
222: second through-hole
223: third through-hole
261: third through-hole plate
271: first through-hole
272: second through-hole
273: third through-hole

What is claimed is:

1. A test device comprising:
a specimen having a circular cross section that accommodates a test target;
a specimen holding part that holds a plurality of the specimens in a row;
a light emitting element in which light is incident on two adjacent specimens among the plurality of specimens held in the specimen holding part;
a first light guide path that guides light emitted by the light emitting element; and
a second light guide path that is formed thinner than the first light guide path and that guides the light emitted by the light emitting element from the first light guide path to the specimen,
wherein the light emitting elements includes
a plurality of first color light emitting elements that emit light of a first color, and
a plurality of second color light emitting elements that emit light of a second color different from the first color, and
the first color light emitting elements and the second color light emitting elements are alternately arranged in an arrangement of the plurality of light emitting elements.

2. The test device according to claim 1,
wherein the first light guide path is provided in common to a plurality of the light emitting elements.

3. The test device according to claim 1,
wherein the second light guide path includes a through-hole parallel to a direction connecting the light emitting element and the specimen.

4. The test device according to claim 2,
wherein the second light guide path includes a through-hole parallel to a direction connecting the light emitting element and the specimen.

5. The test device according to claim 1,
wherein the second light guide path has a configuration in which a plurality of plates having through-holes are disposed so that light penetrates in parallel to a direction connecting the light emitting element and the specimen.

6. The test device according to claim 2,
wherein the second light guide path has a configuration in which a plurality of plates having through-holes are disposed so that light penetrates in parallel to a direction connecting the light emitting element and the specimen.

7. The test device according to claim 1, further comprising:
a light-receiving element that receives light transmitted or scattered by the specimen for each specimen.

8. The test device according to claim 2, further comprising:
a light-receiving element that receives light transmitted or scattered by the specimen for each specimen.

9. The test device according to claim 3, further comprising:
a light-receiving element that receives light transmitted or scattered by the specimen for each specimen.

10. The test device according to claim 4, further comprising:
a light-receiving element that receives light transmitted or scattered by the specimen for each specimen.

11. The test device according to claim 7,
wherein in the light emitting element, light is incident from an oblique direction with respect to a direction connecting the light-receiving element and the specimen and orthogonal in an arrangement direction of specimen in the specimen holding part.

12. The test device according to claim 7,
wherein the light-receiving element includes a shielding member that limits incidence of light, and receives light transmitted or scattered by the specimen through an opening of the shielding member.

13. The test device according to claim 12, wherein the opening has a shape long in an arrangement direction of the light emitting elements.

14. The test device according to claim 12, wherein the opening includes a color filter that selectively transmits light emitted by the light emitting element.

15. The test device according to claim 14, wherein the opening is divided into a plurality of regions, and includes the color filter in which a color of the transmitted light is different for each region.

16. The test device according to claim 1, further comprising:
a third color light emitting element that emits light of a third color different from the first color and the second color, and in which light is incident from a direction connecting the light-receiving element and the specimen and orthogonal in an arrangement direction of specimen in the specimen holding part, between the first color light emitting element and the second color light emitting element, in addition to the light emitting element.

17. A test device comprising:
a plurality of measuring units that includes a specimen having a circular cross section which accommodates a test target, a specimen holding part which holds a plurality of the specimens in a row, a light emitting element in which light is incident on two adjacent specimens among the plurality of specimens, a first light guide path which guides light emitted by the light emitting element, and a second light guide path formed to have a smaller diameter than a diameter of the first light guide path and which guides the light emitted by the light emitting element from the first light guide path to the specimen,
wherein the light emitting elements includes
a plurality of first color light emitting elements that emit light of a first color, and
a plurality of second color light emitting elements that emit light of a second color different from the first color, and
the first color light emitting elements and the second color light emitting elements are alternately arranged in an arrangement of the plurality of light emitting elements.

* * * * *